United States Patent [19]

Hellberg et al.

[11] Patent Number: 5,051,420
[45] Date of Patent: Sep. 24, 1991

[54] 4-SUBSTITUTED-3-1H-IMIDAZOL-1-,2,5-THIADIAZOLES AS ANTIARRHYTHMIC AGENTS

[75] Inventors: Mark R. Hellberg, Arlington, Tex.; James R. Shanklin, Jr., Richmond, Va.

[73] Assignee: A. H. Robins Company, Incorporated, Richmond, Va.

[21] Appl. No.: 664,306

[22] Filed: Mar. 4, 1991

[51] Int. Cl.$^5$ ............... A61K 31/41; A61K 31/535; C07D 417/04

[52] U.S. Cl. .................. 514/236.2; 514/210; 514/212; 514/252; 514/326; 514/362; 540/603; 544/134; 544/368; 546/209; 548/135

[58] Field of Search ............. 540/603; 544/134, 368; 546/209; 548/135; 514/210, 212, 236.2, 252, 326, 362

[56] References Cited

U.S. PATENT DOCUMENTS 3,729,469  4/1973  Wasson ..................... 548/135

Primary Examiner—Robert W. Ramsuer
Attorney, Agent, or Firm—Walter Patton

[57] ABSTRACT

Invention compounds of the formula:

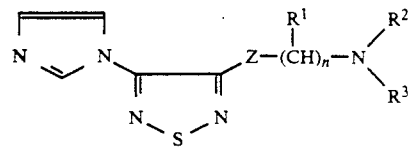

wherein Z is

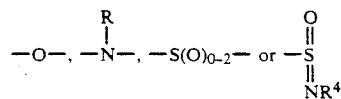

are novel.

Compounds of the above formula have shown antiarrhythmic activity in an electrophysiological assay.

5 Claims, No Drawings

4-SUBSTITUTED-3-1H-IMIDAZOL-1-,2,5-THIADIAZOLES AS ANTIARRHYTHMIC AGENTS

BACKGROUND OF THE INVENTION

1. Field of Invention

Novel 4-substituted-3-(1H-1-imidazlyl)-1,2,5-thiadiazoles have been found to have Class III antiarrhythmic activity as evidenced in electro-physiological in vitro tests.

2. Information Disclosure Statement

The compounds of this invention are unique. The closest structurally related antiarrhythmic compounds are the subject of the European patent 0306440 A2 and are represented by the formula:

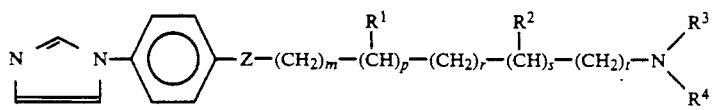

where Z is

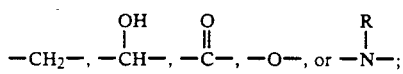

m, p, r, s, and t are 0 or 1; and the various R groups are selected from H, alkyl, cycloalkyl, aryl and combinations thereof, or two R groups can be combined to form a saturated carbocyclic or heterocyclic ring.

SUMMARY OF THE INVENTION

The compounds of this invention are represented by Formula I wherein Z is as defined below:

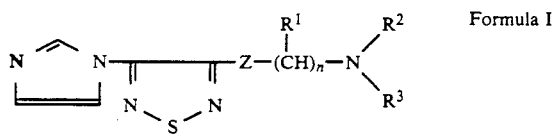

Formula I

Z is

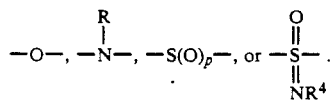

Under Formula I, n is 2-4, p is 0, 1, or 2; R and $R^1$ are independently H or $C_1$-$C_4$ alkyl; $R^2$ and $R^3$ are selected from H or $C_1$-$C_4$ alkyl, aryl, arylalkyl, or $R^1$ and $R^2$ are joined to form a saturated 4 to 6 membered heterocyclic ring such as azetidine, pyrrolidine or piperidine or $R^2$ and $R^3$ are joined to form a saturated 4 to 6 membered heterocyclic ring which may contain an additional heteroatom such as azetidine, pyrrolidine, piperidine, piperazine, or morpholine. $R^4$ is H, $C_1$-$C_6$ alkyl, arylalkyl, $C_1$-$C_4$ alkoxycarbonyl, benzyloxycarbonyl, $C_1$-$C_4$ alkylcarbonyl, $C_1$-$C_4$ alkylaminocarbonyl, or phenylaminocarbonyl; and the pharmaceutically acceptable salts thereof.

In a further definition of terms, $C_1$-$C_4$ alkyl includes the straight and branched chain alkyl groups methyl, ethyl, n-propyl, isopropyl, n-butyl, t-butyl, and sec-butyl. Aryl is phenyl or phenyl substituted by halogen, $C_1$-$C_4$ alkyl, nitro, amino, $C_1$-$C_4$ alkylamino, $C_1$-$C_4$ dialkylamino, or $CF_3$. Arylalkyl is benzyl or phenyl-ethyl. The term pharmaceutically acceptable salt includes hydrates, solvates, and acid addition salts which may be prepared from a Formula I compound and an inorganic or organic acid, including, but not limited to, hydrochloric acid, sulfuric acid, phosphoric acid, maleic acid, fumaric acid, hexamic acid, citric acid, tartaric acid, methanesulfonic acid, and the like.

The Class III antiarrhythmic activity was determined in vitro by measuring cellular electrophysiologic effects in canine Purkinje fibers where prolongation of the action potential duration at 50% and 90% repolarization is indicative of a Class III antiarrhythmic agent.

DETAILED DESCRIPTION OF THE INVENTION

The Formula I compounds of this invention are prepared according to the following reaction schemes:

Scheme A:

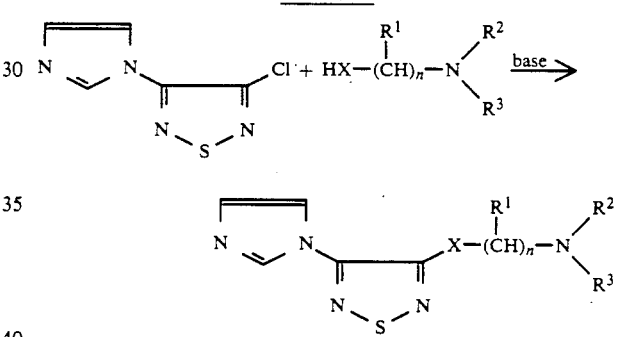

In scheme A, X is O or S. The base used can be an alkyllithium such as butyllithium, sodium hydride or a sodium alkoxide such as sodium methoxide with sodiumhydride being more commonly used. An anhydrous aprotic solvent such as dimethylformamide or tetrahydrofuran is commonly used but other dry aprotic solvents can be used.

Scheme B:

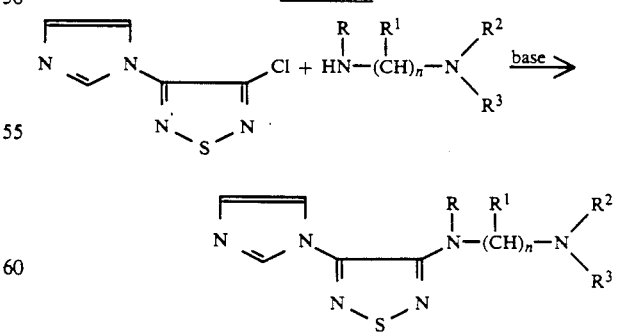

The preparation of Formula I compounds from primary or secondary amines of the formula NHR-(CHR$^1$)n-NR$^2$R$^3$ is accomplished by stirring together the amine and 3-chloro-4-(1H-imidazol-1-yl)-1,2,5-thiadiazole neat, if the amine is a liquid, or in a solvent, such as n-butanol, methylethyl ketone, or dimethylformamide, usually in the presence of an acid acceptor such as sodium bicarbonate or potassium carbonate, at room temperature or up to the boiling point of the solvent.

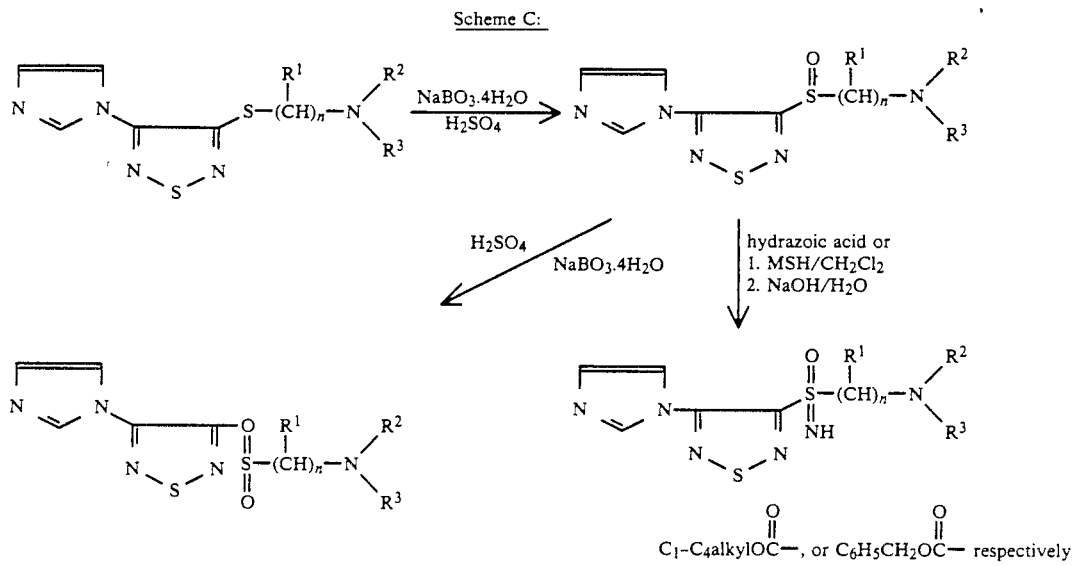

Sulfides prepared according to Scheme A are oxidized to the sulfoxide or sulfone using sodium perborate in an acidic medium which prevents the terminal amino group from being oxidized. Sulfoxides are obtained from the perborate oxidation under relatively mild conditions (room temperature or less) whereas sulfones are obtained under reaction conditions at higher temperatures. Sulfoximines are obtained by reaction of a sulfoxide with hydrazoic acid or treatment with o-mesitylenesulfonylhydroxylamine (Synthesis, 1, Jan. 1977, pp. 1-17).

Substituted sulfoximines ($R^4$ is not H) are prepared by alkylation or acylation reactions as outlined in Scheme D.

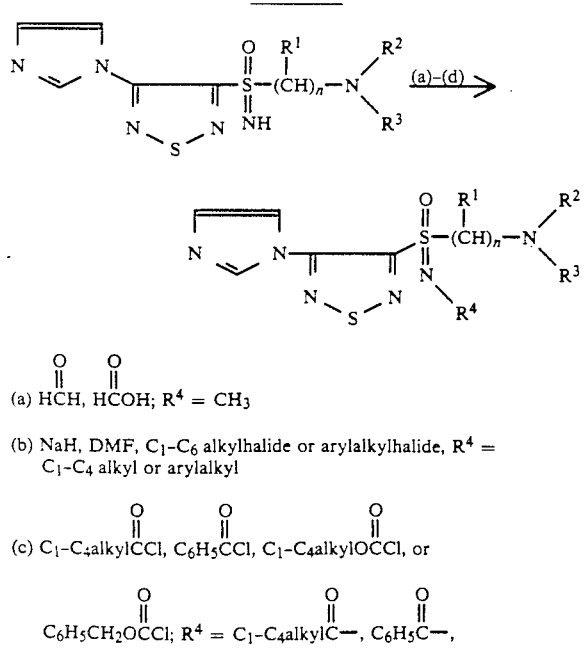

(a) HCH, HCOH; $R^4$ = $CH_3$ (b) NaH, DMF, $C_1$-$C_6$ alkylhalide or arylalkylhalide, $R^4$ = $C_1$-$C_4$ alkyl or arylalkyl (c) $C_1$-$C_4$alkylCCl, $C_6H_5$CCl, $C_1$-$C_4$alkylOCCl, or $C_6H_5CH_2OCCl$; $R^4$ = $C_1$-$C_4$alkylC—, $C_6H_5C$—, $C_1$-$C_4$alkylOC—, or $C_6H_5CH_2OC$— respectively (d) $C_1$-$C_4$alkylNCO; $R^4$ = $C_1$-$C_4$alkylNHC—

Method (a) is the Eschweiler-Clarke procedure. Method (b) is the procedure reported in Aust. J. Chem., 1986, 39, 1655-9. Methods (c) and (d) are acylation reacitons carried out in anhydrous aprotic solvents such as methylene chloride or tetrahydrofuran. In method (c) an acid acceptor such as triethylamine or sodium or potassium carbonate may be added.

The above reaction schemes are broadly described and are not to be construed as limiting to this disclosure. In the above reaction, standard laboratory conditions and practices are used for the preparation, isolation, and purification of the invention compounds and one skilled in the art should be able to practice this invention without undue experimentation. The following are specific examples of preparations of compounds of the present invention.

PREPARATION 1

3-Chloro-4-(1H-imidazol-1-yl)-1,2,5-thiadiazole hydrochloride (1:1)

Imidazole (4.38 g, 64.4 mmol) was warmed to 100° C. To the liquid imidazole was added 3,4-dichloro-1,2,5-thiadiazole (5.00 g, 32.2 mmol), dropwise. The resulting solution was warmed at 110° C. for 1 h and at 125° C. for 4 h. The mixture was cooled to ambient temperature and was partitioned between $H_2O$ (50 mL) and methylene chloride. The layers were separated, and the aqueous layer was extracted with methylene chloride (2 × 50 mL). The combined organics were dried ($MgSO_4$) and concentrated in vacuo to give 4.1 g of residue. The residue was chromatographed (flash, $SiO_2$, 98:2 methylene chloride:methanol) to give 1.05 g of product (17.5% crude yield). A 0.5-g sample was dissolved in ether and treated with ethereal HCl. A small amount of ethanol was added, and the white solid that formed was collected by filtration to obtain 0.61 g (17.5% yield), mp 219°-220° C.

Analysis: Calculated for $C_5H_3N_4SCl \cdot HCl$: C, 26.92; H, 1.81; N, 25.12. Found: C, 26.72; H, 1.82; N, 24.77.

EXAMPLE 1

N,N-Diethyl-3-[4-(1H-imidazol-1-yl)-1,2,5-thiadiazol-3-yloxy]-1-propanamine hydrochloride (1:1)

A solution of 3-diethylamino-1-propanol (1.55 g, 11.8 mmol) in tetrahydrofuran (10 mL) was added dropwise to a slurry of sodium hydride (60% oil dispersion, 0.47 g, 11.8 mmol, washed 3×20 mL hexane) in tetrahydrofuran (10 mL) maintained at 0° C. After 0.5 h a solution of 3-chloro-4-(1H-imidazol-1-yl)-1,2,5-thiadiazole (2.20 g, 11.8 mmol) in tetrahydrofuran (10 mL) was added dropwise at 0° C. The reaction mixture was stirred at 0° C. for 1 h and at ambient temperature for 16 h. Water (1 mL) was added to the reaction mixture, and the resulting mixture was concentrated in vacuo. The residue was partitioned between water (30 mL) and methylene chloride (30 mL). The layers were separated, and the aqueous layer was extracted with methylene chloride (2×30 mL). The combined organic extracts were dried (MgSO$_4$) and concentrated to give 2.9 g of residue. The residue was chromatographed (flash, SiO$_2$, 9:1 methylene chloride/methanol) to give 1.10 g (33% crude yield) of crude product. This was dissolved in an ethanol-ether mixture and treated with ethereal HCl. The white solid which formed was collected by filtration to obtain 0.81 g (19.4%), mp 167°–168° C.

Analysis: Calculated for $C_{12}H_{19}N_5OS \cdot HCl$: C, 40.68; H, 5.97; N, 19.77. Found: C, 40.41; H, 6.19; N, 19.62.

EXAMPLE 2

N,N-Diethyl-2-[4-(1H-imidazol-1-yl)-1,2,5-thiadiazol-3-yloxy)]ethanamine hydrochloride (1:2)

A solution of 2-diethylaminoethanol (2.20 g, 18.7 mmol) in tetrahydrofuran (10 mL) was added to a slurry of sodium hydride (60% oil dispersion, 0.80 g, 20.0 mmol), washed 3×10 mL hexane) in tetrahydrofuran (10 mL) maintained at 0° C. The resulting mixture was stirred for 15 minutes at 0° C. and 45 minutes at ambient temperature. The reaction mixture was cooled to 0° C., and a solution of 3-chloro-4(1H-imidazol-1-yl)-1,2,5-thiadiazole (2.9 g, 15.6 mmol) in tetrahydrofuran (10 mL) was added dropwise. After the addition was complete, the reaction mixture was stirred at ambient temperature for 3 h. Water (2 mL) was added, and the resulting solution was concentrated in vacuo. The residue was partitioned between water (50 mL) and methylene chloride (50 mL). The layers were separated and the water layer extracted with methylene chloride (50 mL). The combined organic extracts were dried (MgSO$_4$) and concentrated in vacuo to give 4.16 g of residue. The residue was chromatographed (flash, SiO$_2$, 9:1, methylene chloride and methanol) to give 2.38 g (57% crude yield) of crude product. The crude product was dissolved in a mixture of ethanol and ether, and the resulting solution was treated with ethereal HCl. The solid that formed was collected by filtration to give 2.20 g (34.6% yield) of white solid, mp 177°–179° C.

Analysis: Calculated for $C_{11}H_{17}N_5OS \cdot HCl$: C, 38.83; H, 5.63; N, 20.58. Found: C, 38.44; H, 5.86; N, 20.28.

EXAMPLE 3

N,N-Di-(1-methylethyl)-2-[4-(4-(1H-imidazol-1-yl)-1,2,5-thiadiazol-3-yloxy]ethanamine Following the procedures of Example 1, the title compound is obtained from 3-chloro-4-(1H-imidazol-1-yl)-1,2,5-thiadiazole and N,N-diisopropylethanolamine.

EXAMPLE 4

N,N-Dimethyl-2-[4-(1H-imidazol-1-yl)-1,2,5-thiadiazol-3-oxy]-1-propanamine

Following the procedures of Example 1, the title compound is obtained from 3-chloro-4-(1H-imidazol-1-yl)-1,2,5-thiadiazol and N,N-dimethyl-2-hydroxy-propanamine.

EXAMPLE 5

4-[2-[4-(1H-Imidazol-1-yl)-1,2,5-thiadiazol-3-yloxy]ethyl]morpholine

Following the procedures of Example 1, the title compound is obtained from 3-chloro-4-(1H-imidazol-1-yl)-1,2,5-thiadiazole and 4-(2-hydroxyethyl)morpholine.

EXAMPLE 6

1-[2-[4-(1H-Imidazol-1-yl)-1,2,5-thiadiazol-3-yloxy]ethyl]pyrrolidine

Following the procedures of Example 1, the title compound is prepared from 3-chloro-4-(1H-imidazol-1-yl)-1,2,5-thiadiazole and 1-(2-hydroxyethyl)pyrrolidine.

EXAMPLE 7

1-Benzyl-2-[[4-(1H-imidazol-1-yl)-1,2,5-thiadiazol-3-yloxy]methyl]pyrrolidine

Following the procedures of Example 1, the title compound is prepared from 3-chloro-4-(1H-imidazol-1-yl)-1,2,5-thiadiazole and 1-benzyl-2-(hydroxymethyl)-pyrrolidine.

EXAMPLE 8

N-benzyl, N-methyl-3-[4-(1H-imidazol-1-yl)-1,2,5-thiadiazol-3-yloxy]-1-propanamine Following the procedures of Example 1, the title compound is prepared from 3-chloro-4-(1H-imidazol-1-yl)-1,2,5-thiadiazole and N-benzyl, N-methyl-3-amino-1-propanol.

EXAMPLE 9

N,N-Diethyl-4-[4-(1H-imidazol-1-yl)-1,2,5-thiadiazol-3-yloxy]-1-pentanamine

Following the procedure of Example 2, the title compound is prepared from 3-chloro-4-(1H-imidazol-1-yl)-1,2,5-thiadiazole and N,N-diethyl-5-hydroxy-1-pentanamine.

EXAMPLE 10

N,N-Diethyl-2-[[4-(1H-imidazol-1-yl)-1,2,5-thiadiazol-3-yl]sulfenyl]-ethanamine

Following the procedures of Example 1, the title compound is prepared from 3-chloro-4-(1H-imidazol-1-yl)-1,2,5-thiadiazole and diethylaminoethanethiol.

EXAMPLE 11

N,N-diethyl-2-[[4-(1H-imidazol-1-yl)-1,2,5-thiadiazol-3-yl]sulfinyl]-ethanamine

A cold (0° C.) solution of the compound of Example 10 in methanol is treated slowly with excess 30% sulfuric acid an then sodium perborate tetrahydrate (10 equivalents) is added. The mixture is stirred at 0° C. for 2 hrs and then at ambient temperature for 2 hrs. The methanol is removed in vacuo and the residue basified with 50% sodium hydroxide and filtered. The filter cake is washed with methylene chloride and the aqueous filtrate extracted with the methylene chloride washings. The combined extract is washed with water, dried, and concentrated to obtain the title compound.

EXAMPLE 12

S-[2-(diethylamino)ethyl]-S-[4-(1H-imidazol-1-yl)-1,2,5-thiadiazol-3-yl]sulfoximine Concentrated sufuric acid (13 ml) is added dropwise to a stirred slurry of the compound of Example 11 (13 mmol) and sodium azide (52 mmol) in chloroform at −20° C. The reaction mixture is allowed to warm to ambient temperature and then heated at reflux temperature for 36 hr. The reaction mixture is then cooled to 0° C. and water (100 ml) added. The mixture is carefully basified with 50% sodium hydroxide solution. The chloroform layer is separated and the aqueous layer is extracted with methylene chloride. The combined organic layers are dried and concentrated to obtain the product which is purified by standard procedures.

EXAMPLE 13

N,N-Diethyl-3-[[4-(1H-imidazol-1-yl)1,2,5-thiadiazol-3-yl]amino]-1-propylamine

A mixture of 3-chloro-4-(1H-imidazol-1-yl)-1,2,5-thiadiazole (0.05 mol) and 3-diethylaminopropylamine (0.50 mol) is heated at 100° C. until the 3-chloro-4-(1H-imidazol-1-yl)-1,2,5-thiadiazole is consumed. Excess 3-diethylamino-propylamine is removed by distillation at reduced pressure and the residue partitioned between methylene chloride and 1N sodium hydroxide solution. The methylene chloride extract is dried and concentrated to obtain the product which is purified by standard procedures.

EXAMPLE 14

N,N-Diethyl-2-[[4-(1H-imidazol-1-yl)-1,2,5-thiadiazol-3-yl]amino]ethylamine

Following the procedures of Example 13 and substituting N,N-diethyl-ethylenediamine for 3-diethylaminopropylamine, the title compound is obtained.

EXAMPLE 15

N,N-Diethyl-2-[[4-(1H-imidazol-1-yl)-1,2,5-thiadiazol-1-yl]methyl-amino]ethylamine Following the procedures of Example 13 and substituting N,N,N'-triethylethylenediamine for 3-diethylaminopropylamine, the title compound is obtained.

EXAMPLE 16

1-[2-[[4-(1H-imidazol-1-yl)-1,2,5-thiadiazol-1-yl]amino]ethyl]piperidine

Following the procedures of Example 13 and substituting 1-(2-aminoethyl)piperidine for 3-diethylaminopropylamine, the title compound is obtained.

EXAMPLE 17

S-[2-(diethylamino)ethyl]-S-[4-(1H-imidazol-1-yl)-1,2,5-thiadiazol-3-yl]-N-[(phenylmethoxy)carbonyl]sulfoximine A mixture of S-[2-(diethylamino)ethyl]-S-[4-(1H-imidazol-1-yl)-1,2,5-thiadiazol-3-yl]sulfoximine (10 mmol), benzyl chloroformate (12 mmol) and potassium carbonate (32 mmol) in methylene chloride is stirred at ambient temperature for 5 hr. The mixture is filtered and the filtrate concentrated to obtain the product which is purified using standard laboratory procedures.

EXAMPLE 18

N-Acetyl-S-[2-(diethylamino)ethyl]-S-[4-(1H-imidazol-1-yl)-1,2,5-thiadiazol-3-yl]sulfoximine Following the procedures of Example 16, the title compound is prepared from acetyl chloride and S-[2-(diethylamino)ethyl]-S-[4-(1H-imidazol-1-yl)-1,2,5-thiadiazol-3-yl]sulfoximine.

EXAMPLE 19

S-[2-(diethylamino)ethyl]-S-[4-(1H-imidazol-1-yl)-1,2,5-thiadiazol-3-yl]-N-methylsulfoximine A mixture of S-[2-(diethylamino)ethyl]-S-[4-(1H-imidazol-1-yl)-1,2,5-thiadiazol-3-yl]sulfoximine (30 mmol), 17 ml of 37% formaldehyde and 22.6 ml of 98% formic acid is heated at reflux temperature for 48 hr. Water is added to the reaction mixture which is then made slightly basic by addition of 50% sodium hydroxide solution. The mixture is extracted with chloroform and the extract is dried and concentrated to obtain the title compound.

TABLE I

| Example | Z | $-(CH)_n-N\begin{smallmatrix}R^1\\R^2\\R^3\end{smallmatrix}$ |
| --- | --- | --- |
| 1 | O | $-(CH_2)_3NEt_2$ |
| 2 | O | $-(CH_2)_2NEt_2$ |
| 3 | O | $-(CH_2)_2NiPr_2$ |
| 4 | O | $-(CH_2)_3NMe_2$ |
| 5 | O | $-(CH_2)_2-N\bigcirc O$ (morpholino) |
| 6 | O | $-(CH_2)_2-N\bigcirc$ (piperidino) |

TABLE I-continued

Structure:
```
   ⎡───⎤         R¹    R²
   N   N          \   /
    ╲ ╱  ═Z─(CH)ₙ─N
     ═             \
    N   N           R³
     ╲S╱
```

R¹    R²
                     \   /
          −(CH)ₙ─N
                     \
                      R³

| Example | Z | −(CH)ₙ−NR¹R²R³ (substituent) |
|---|---|---|
| 7 | O | −CH₂−[pyrrolidine N-CH₂C₆H₅] |
| 8 | O | −(CH₂)₃N(CH₃)(CH₂C₆H₅) |
| 9 | O | −(CH₂)₅NEt₂ |
| 10 | S | −(CH₂)₂NEt₂ |
| 11 | O=S | −(CH₂)₂NEt₂ |
| 12 | O=S=NH | −(CH₂)₂NEt₂ |
| 13 | NH | −(CH₂)₃NEt₂ |
| 14 | NH | −(CH₂)₂NEt₂ |
| 15 | NCH₃ | −(CH₂)₂NEt₂ |
| 16 | NH | −(CH₂)₂N−(cyclohexyl) |
| 17 | O=S=NCOCH₂C₆H₅(=O) | −CH₂CH₂NEt₂ |
| 18 | O=S=NCCH₃(=O) | −CH₂CH₂NEt₂ |
| 19 | O=S=N−CH₃ | −CH₂CH₂NEt₂ |

PHARMACOLOGY AND PHARMACEUTICAL METHODS

Measurement of Cellular Electrophysiologic Effects in Canine Purkinje Fibers In Vitro Dogs (12-18 Kg) were anesthetized with sodium pentobarbital (30 mg/kg IV). The heat of each dog was rapidly removed through a right lateral thoracotomy and placed in a chilled, oxygenated Tyrode's solution. Purkinje fibers from the right and left ventricles were excised and mounted in a Lucite chamber. The tissue was superfused at a rate of 10-15 ml/min with Tyrode's solution. The temperature of the superfused Tyrode's was maintained at 37° C. and gassed with 95% oxygen-5% carbon dioxide mixture.

The Purkinje fibers were stimulated (paced at cycle length of 400 to 1000 msec) with a silver bipolar wire electrode placed on the surface of the tissue. Transmembrane action potentials were recorded with a glass capillary microelectrodes filled with 3M KCl. The action potentials were displayed on a Tectronix 5113 oscilloscope. The measurements derived from the action potential were Vmax (upstroke velocity), APD50 (action potential duration at 50% repolarization), and APD90 (action potential duration at 90% repolarization) as previously described (Bigger and Mandel, 1970; Wu and Hoffman, 1987). Test compounds were added to the reservoir of Tyrode's solution to concentrations of 10 and 100 uM. Measurements of the action potential parameters were recorded after 20 min of test drug exposure. These measurements were compared to those obtained prior to the test compound. Changes in the action potential measurements produced by the test compound were analyzed for statistical significance using a paired-t test. A minimum of 3 tissues were used for each test compound.

Bigger J. T. and Mandel W. J. Effects of lidocaine on the electrophysiologic properties of ventricular muscle and Purkinje fibers. J. CLIN. INVEST. Vol 49: 63-77 (1970).

Wu K. M. and Hoffman B. F. Effect of procainamide and N-acetylprocainamide on atrial flutter; studies in vivo and in vitro. CIRCULATION Vol 76: 1397-1408 (1987).

TABLE II

| | | Electrophysiological Data | |
|---|---|---|---|
| | Conc. (M) | ADP$_{90}$ (% change) | ADP$_{50}$ (% change) |
| Ex. 1 | $10^{-5}$ | 15.6 | 2.3 |
| | $10^{-4}$ | 17.6 | 20.2 |
| Ex. 2 | $10^{-5}$ | 3.4 | 4.4 |
| | $10^{-4}$ | 17.8 | 23.8 |

Generally, the method of treating cardiac arrhythmia in accordance with this invention comprises administering internally to warm-blooded animals, including human beings, a therapeutically effective amount of a compound of Formula I or a pharmaceutically acceptable salt in a wide variety of pharmaceutical forms well known in the art, preferably with a non-toxic pharmaceutical carrier. The active agent is administered orally, subcutaneously, intravenously, or intramuscularly and, if necessary, in repeated dosages until satisfactory response is obtained. Compositions for oral adminstration can take the form of elixirs, capsules, tablets, or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone. For parenteral administration, the carrier or excipient can be comprised of a sterile parenterally acceptable liquid, e.g., water or arachis oil contained in ampoules.

The effective antiarrhythmic dose of a Formula I compound in warm-blooded animals is expected to be in the range of from 0.01 to 100 mg/kg and will further depend on the compound and the route of administration.

In all of the above, it is only necessary that a suitable effective dosage be consistent with the dosage form employed. The exact individual dosages, as well as the daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A compound possessing antiarrhythmic properties of the formula:

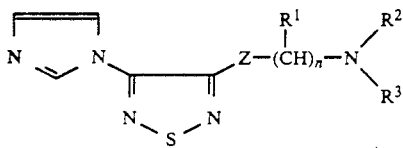

wherein Z is

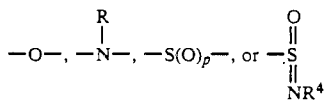

where n is 2-4, p is 0, 1 or 2; R and $R^1$ are independently H or $C_1$-$C_4$ alkyl; $R^2$ and $R^3$ are selected from H, $C_1$-$C_4$ alkyl, aryl, arylalkyl, or $R^1$ and $R^2$ are joined to form a saturated 4-6 membered heterocyclic ring or $R^2$ and $R^3$ are joined to form a 4-6 membered heterocyclic ring which may contain an additional heteroatom; $R^4$ is H, $C_1$-$C_6$ alkyl, arylalkyl, $C_1$-$C_4$ alkoxycarbonyl, benzyloxycarbonyl, $C_1$-$C_4$ alkylcarbonyl, $C_1$-$C_4$ alkylaminocarbonyl, or arylaminocarbonyl; or a pharmaceutically acceptable salt thereof.

2. A compound according to claim 1 which is selected from:
N,N-Diethyl-2-[4-(1H-imidazol-1-yl)-1,2,5-thiadiazol-3-yloxy]ethanamine;
N,N-Di-(1-methylethyl)-2-[4-(4-(1H-imidazol-1-yl)-1,2,5-thiadiazol-3-yloxy]ethanamine;
N,N-Dimethyl-2-[4-(1H-imidazol-1-yl)-1,2,5-thiadiazol-3-yloxy]-1-propanamine;
4-[2-[4-(1H-Imidazol-1-yl)-1,2,5-thiadiazol-3-yloxy]ethyl]morpholine;
1-[2-[4-(1H-Imidazol-1-yl)-1,2,5-thiadiazol-3-yloxy]ethyl]pyrrolidine;
1-Benzyl-2-[[4-(1H-imidazol-1-yl)-1,2,5-thiadiazol-3-yloxy]-methyl]pyrrolidine;
N-Benzyl, N-methyl-3-[4-(1H-imidazol-1-yl)-1,2,5-thiadiazol-3-yloxy]-1-propanamine;
N,N-Diethyl-4-[4-(1H-imidazol-1-yl)-1,2,5-thiadiazol-3-yloxy]-1-pentanamine;
N,N-Diethyl-2-[[4-(1H-imidazol-1-yl)-1,2,5-thiadiazol-3-yl]sulfenyl]-ethanamine;
N,N-Diethyl-2-[[4-(1H-imidazol-1-yl)-1,2,5-thiadiazol-3-yl]sulfinyl]-ethanamine;
S-[2-(Diethylamino)ethyl]-S-[4-(1H-imidazol-1-yl)-1,2,5-thiadiazol-3-yl]sulfoximine;
N,N-Diethyl-3-[[4-(1H-imidazol-1-yl)1,2,5-thiadiazol-3-yl]amino]-1-propylamine;
N,N-Diethyl-2-[[4-(1H-imidazol-1-yl)-1,2,5-thiadiazol-3-yl]amino]ethylamine;
N,N-Diethyl-2-[[4-(1H-imidazol-1-yl)-1,2,5-thiadiazol-3-yl]methyl-amino]ethylamine;
1-[2-[[4-(1H-Imidazol-1-yl)-1,2,5-thiadiazol-3-yl]amino]ethyl]piperidine;
S-[2-(Diethylamino)ethyl]-S-[4-(1H-imidazol-1-yl)-1,2,5-thiadiazol-3-yl]-N-[(phenylmethoxy)carbonyl]-sulfoximine;
N-Acetyl-S-[2-(diethylamino)ethyl]-S-[4-(1H-imidazol-1-yl)-1,2,5-thiadiazol-3-yl]sulfoximine;
S-[2-(Diethylamino)ethyl]-S-[4-(1H-imidazol-1-yl)-1,2,5-thiadiazol-3-yl]-N-methylsulfoximine;
or a pharmaceutically acceptable salt thereof.

3. A method of treating certain cardiac arrhythmias by internally administering to a warm-blooded animal in need thereof a therapeutically effective amount of a compound according to the formula:

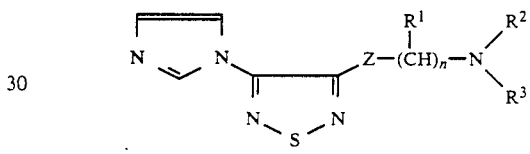

wherein Z is

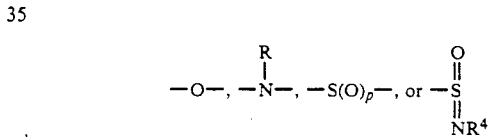

where n is 2-4, p is 0, 1 or 2; R and $R^1$ are independently H or $C_1$-$C_4$ alkyl; $R^2$ and $R^3$ are selected from H, $C_1$-$C_4$ alkyl, aryl, arylalkyl, or $R^1$ and $R^2$ are joined to form a saturated 4-6 membered heterocyclic ring or $R^2$ and $R^3$ are joined to form a 4-6 membered heterocyclic ring which may contain an additional heteroatom; $R^4$ is H, $C_1$-$C_6$ alkyl, arylalkyl, $C_1$-$C_4$ alkoxycarbonyl, benzyloxycarbonyl, $C_1$-$C_4$ alkylcarbonyl, $C_1$-$C_4$ alkylaminocarbonyl, or arylaminocarbonyl; or a pharmaceutically acceptable salt thereof.

4. A method of treating certain cardiac arrhythmias by internally administering to a warm-blooded animal in need thereof a therapeutically effective amount of a compound selected from the compounds group consisting of:
N,N-Diethyl-2-[4-(1H-imidazol-1-yl)-1,2,5-thiadiazol-3-yloxy]ethanamine;
N,N-Di-(1-methylethyl)-2-[4-(4-(1H-imidazol-1-yl)-1,2,5-thiadiazol-3-yloxy]ethanamine;
N,N-Dimethyl-2-[4-(1H-imidazol-1-yl)-1,2,5-thiadiazol-3-yloxy]-1-propanamine;
4-[2-[4-(1H-Imidazol-1-yl)-1,2,5-thiadiazol-3-yloxy]ethyl]morpholine;
1-[2-[4-(1H-Imidazol-1-yl)-1,2,5-thiadiazol-3-yloxy]ethyl]pyrrolidine;
1-Benzyl-2-[[4-(1H-imidazol-1-yl)-1,2,5-thiadiazol-3-yloxy]-methyl]pyrrolidine;

N-Benzyl, N-methyl-3-[4-(1H-imidazol-1-yl)-1,2,5-thiadiazol-3-yloxy]-1-propanamine;

N,N-Diethyl-4-[4-(1H-imidazol-1-yl)-1,2,5-thiadiazol-3-yloxy]-1-pentanamine;

N,N-Diethyl-2-[[4-(1H-imidazol-1-yl)-1,2,5-thiadiazol-3-yl]sulfenyl]-ethanamine;

N,N-Diethyl-2-[[4-(1H-imidazol-1-yl)-1,2,5-thiadiazol-3-yl]sulfinyl]-ethanamine;

S-[2-(Diethylamino)ethyl]-S-[4-(1H-imidazol-1-yl)-1,2,5-thiadiazol-3-yl]sulfoximine;

N,N-Diethyl-3-[[4-(1H-imidazol-1-yl)1,2,5-thiadiazol-3-yl]amino]-1-propylamine;

N,N-Diethyl-2-[[4-(1H-imidazol-1-yl)-1,2,5-thiadiazol-3-yl]amino]ethylamine;

N,N-Diethyl-2-[[4-(1H-imidazol-1-yl)-1,2,5-thiadiazol-3-yl]methyl-amino]ethylamine;

1-[2-[[4-(1H-Imidazol-1-yl)-1,2,5-thiadiazol-3-yl]amino]ethyl]piperidine;

S-[2-(Diethylamino)ethyl]-S-[4-(1H-imidazol-1-yl)-1,2,5-thiadiazol-3-yl]-N-[(phenylmethoxy)carbonyl]-sulfoximine;

N-Acetyl-S-[2-(diethylamino)ethyl]-S-[4-(1H-imidazol-1-yl)-1,2,5-thiadiazol-3-yl]sulfoximine;

S-[2-(Diethylamino)ethyl]-S-[4-(1H-imidazol-1-yl)-1,2,5-thiadiazol-3-yl]-N-methylsulfoximine;

or a pharmaceutically acceptable salt thereof.

5. A pharmaceutical composition for the treatment of certain cardiac arrhythmias in warm-blooded animals comprised of:

a. a therapeutically effective amount of a compound according to the formula:

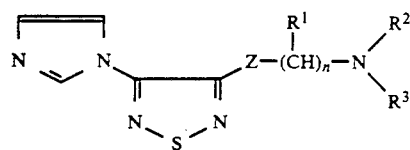

wherein Z is

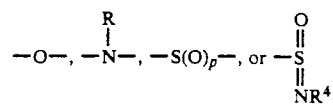

where n is 2–4, p is 0, 1 or 2; R and $R^1$ are independently H or $C_1$–$C_4$ alkyl; $R^2$ and $R^3$ are selected from H, $C_1$–$C_4$ alkyl, aryl, arylalkyl, or $R^1$ and $R^2$ are joined to form a saturated 4–6 membered heterocyclic ring or $R^2$ and $R^3$ are joined to form a 4–6 membered heterocyclic ring which may contain an additional heteroatom; $R^4$ is H, $C_1$–$C_6$ alkyl, arylalkyl, $C_1$–$C_4$ alkoxycarbonyl, benzyloxycarbonyl, $C_1$–$C_4$ alkylcarbonyl, $C_1$–$C_4$ alkylaminocarbonyl, or arylaminocarbonyl; or a pharmaceutically acceptable salt thereof, and b. a pharmaceutical carrier thereof.

* * * * *